(12) United States Patent
Klein

(10) Patent No.: US 6,277,392 B1
(45) Date of Patent: Aug. 21, 2001

(54) TISSUE INJECTABLE COMPOSITION

(75) Inventor: Dean A. Klein, North Oaks, MN (US)

(73) Assignee: Carbon Medical Technologies, Inc., St. Paul, MN (US)

( * ) Notice: Subject to any disclaimer, the term of this patent is extended or adjusted under 35 U.S.C. 154(b) by 0 days.

(21) Appl. No.: 09/397,709

(22) Filed: Sep. 16, 1999

(51) Int. Cl.⁷ .................................................... A61F 2/28
(52) U.S. Cl. ........................ 424/426; 523/113; 523/114; 623/14
(58) Field of Search .................... 424/423, 426; 523/113, 114; 623/14

(56) References Cited

U.S. PATENT DOCUMENTS

| | | | |
|---|---|---|---|
| 4,803,075 | 2/1989 | Wallace et al. | 424/423 |
| 5,007,940 | 4/1991 | Berg | 623/66 |
| 5,116,387 | 5/1992 | Berg | 623/66 |
| 5,158,573 | 10/1992 | Berg | 623/66 |
| 5,204,382 | 4/1993 | Wallace et al. | 523/115 |
| 5,258,028 | 11/1993 | Ersek et al. | 623/11 |
| 5,451,406 | 9/1995 | Lawin et al. | 424/423 |
| 5,792,478 | * 8/1998 | Lawin et al. | 424/502 |

* cited by examiner

Primary Examiner—Carlos A. Azpuru
(74) Attorney, Agent, or Firm—Nawrocki, Rooney & Sivertson, P.A.

(57) ABSTRACT

An improved biocompatible composition consisting of physiologically-stable, isotropic carbon beads or particles carried in a lubricative suspension, solution, other fluid or gel. The composition is intended to be delivered into the body through a small-bored needle, cannula, or other catheter into a tissue site for the purpose of augmenting the tissue. In particular, the composition is useful for augmenting tissue in the area of the cardiac orifice of the stomach to reduce gastric reflux, in the area of the internal or external sphincter of the anal canal to reduce fecal incontinence or in the area of urethral tissue for the purpose of treating urinary incontinence.

20 Claims, 1 Drawing Sheet

FIG.

TISSUE INJECTABLE COMPOSITION

TECHNICAL FIELD

This invention relates to an injectable composition of physiologically compatible and appropriately sized particles carried in a lubricative, biologically compatible fluid of gel. The composition is formulated to be delivered into a body to a tissue site through a small-bore instrument to strengthen, build-up and otherwise augment the tissue site and surrounding area.

BACKGROUND OF THE INVENTION

The percutaneous injection of substances into tissues to augment, support, or reconfigure anatomic structure has been the subject of significant research and development and is well known in the art. See, for example, U.S. Pat. Nos. 4,803,075 and 5,204,382 to Wallace et al., and U.S. Pat. No. 5,258,028 to Ersek et al. Procedures have been described in the medical literature for correction of dermatological, otolaryngological problems and for treatment of urological disorders, e.g., Smith et al., "Evaluation of Polydimethylsiloxane as an Alternative in the Endoscopic Treatment of Vesicoureteral Reflux", *J. Urol.*, 152: 1221–1224, 1994, and Walker et al., "Injectable Bioglass as a Potential Substitute for Injectable: Polytetrafluorethylene", *J Urol.*, 148:645–7 (1992) and the references cited therein.

Urinary incontinence and vesicourethral reflux are urological disorders that have responded to treatments with augmentative materials. Incontinence occurs when the resistance to urine flow has decreased to the point where the resistance can no longer resist the intra-abdominal pressure. Nearly all procedures developed to restore continence are based on restoring the lost resistance to urine outflow. U.S. Pat. Nos. 5,007,940; 5,158,573; and 5,116,387 to Berg disclose biocompatible compositions comprising discrete, polymeric and silicone rubber bodies injectable into urethral tissue for the purpose of treatment of urinary incontinence by tissue bulking. Further, U.S. Pat. No. 5,452,406 to Lawin discloses biocompatible compositions comprising carbon coated substrate particles injectable into a tissue, such as the tissues of and that overlay the urethra and bladder neck, for the purpose of treatment of urinary incontinence by tissue bulking.

The most serious adverse effects that may occur from therapies of this type relate to the migration of the solid materials from the original site of placement into repository sites in various body organs and the chronic inflammatory response of tissue to particles that are too small. These adverse effects are well documented in the urologic literature, specifically in Malizia, A. A. et al., "Migration and Granulomatous Reaction After Periurethral Injection of Polytef (Teflon)", *JAMA* 251:3277–3281 (1984) and Claes, H., Stroobants, D. et al., "Pulmonary Migration Following Periurethral Polytetrafluoroethylene Injection For Urinary Incontinence", *J. Urol.*, 142:821–822 (1989). An important factor in assuring the absence of migration is the administration of properly sized particles. If the particle is too small, it can be engulfed by the body's white cells (phogocytes) and carried to distant organs or be carried away in the microvasculature and travel until it reaches a site of greater constriction. Target organs for deposition include the lungs, liver, spleen, brain, kidney, and lymph nodes.

The use of small diameter particulate spheres, in the range of 1–20 microns, formed of materials such as cross linked collagen or synthetic polymers suspended in an aqueous medium having biocompatible lubricant has been disclosed in Wallace et al., U.S. Pat. No. 4,803,075. While these materials showed positive, short term augmentation results, this result was short lived as the material had a tendency to migrate and/or be absorbed by the host tissue. Teflon paste was used early to treat stress urinary incontinence. Politano, V. S., Small, M. P., Harper, J. M., Lynne, C. M., "Periurethral Teflon Injection for Urinary Incontinence", *J. Urol.*, 111:180–183 (1974). The Teflon paste consisted of Polytetrafluoroethylene particles in a size range of 1 to 100 microns. More than ninety percent of the particles were in the range of 1 to 40 microns. Malizia, A. A. Reiman, H. M., Myers, R. P. et al., "Migration and Granulomatous Reaction After Periurethral Injection of Polytef (Teflon)", *JAMA*, 251:24:3277–3281 (1984). This product demonstrated foreign body granuloma formation at the injection site and local migration. Boedts, D., Roels, H., Kluyskens, P., "Laryngeal Tissue Responses to Teflon", *Arch Otolarynqol*, 86:562–567 (1967).

Proper particle size selection is important. Studies indicate that a particle size for Teflon (PTFE) in the range of between 1 and 100 microns is unacceptable for injectable material. Particles in this size range show local and distant migration, produce chronic inflammatory responses in tissue, and has been associated with clinical complications. Particles that are too large are difficult to deposit e.g. will not go down a needle small enough to have clinical application.

U.S. Pat. No. 5,792,478 to Lawin, issued Aug. 11, 1998, assigned to the assignee of the present invention, discusses pure carbon beads (either graphite or pyrolytic carbon substrate material) which is coated with pyrolytic carbon to form a pure carbon bead and a B-glucan carrier gel.

The primary focus of the present invention has been directed toward the development of improved biocompatible, nonmigratory particles that are effectively delivered to the desired tissue site in an improved lubricative, biocompatible fluid or gel carrier. The preferred carrier shall not cause any deleterious effects from the site by normal biological or biochemical processes such as excretion or metabolic breakdown.

SUMMARY OF THE INVENTION

In accordance with the present invention there is provided an injectable, biocompatible composition comprised of a plurality of discrete, physiologically compatible, isotropic pyrolytic carbon particles of a predetermined size range and a lubricative fluid or gel in which the particles are carried. The carrier is preferably a biologically compatible solution or suspension. The particles range in size from 90 to 1,000 microns in transverse, cross-sectional dimension.

The composition is designed to be delivered into the body through a small-bore needle, cannula, or catheter to a tissue site for the purpose of augmenting the tissue site and surrounding area, thereby correcting a defect, filling a void or strengthening the support structures of the tissue.

The invention is comprised of two components. The first is a plurality of low temperature isotropic (LTI) pyrolytic carbon particles ranging in size as microbeads or microparticles from a minimum of 90 microns to a maximum of 1,000 microns. The LTI particles are created, utilizing the pyrolytic process, to coat a preferred deposition material with LTI carbon. After the pyrolytic process is completed, the pyrolytic carbon is removed from the deposition material by milling, grinding, machining or otherwise to produce particles of the desired particle size. The resulting pure pyrolytic carbon particles are cleaned and sieved to provide particles of the desired size and shape.

The second component acts as the lubricative carrier for the LTI carbon particles and is comprised of a suspension, solution, or other biologically compatible fluid or a gel. The preferred embodiment is a gel of B-glucan with the addition of agarose to form a self supporting gel. Other lubricative carriers can include undiluted agarose, hyaluronic acid and derivatives thereof, polyvinyl pyrrolidone or a hydrogel derivative thereof, dextran or hydrogen derivatives thereof, glycerol, polyethylene glycol, succinylated collagen, liquid collagen, and other polysaccharide or biocompatible polymers, either singly or in combination with one or more of the above-referenced solutions. The carrier must be capable of being formulated into a viscous fluid or into a self-supporting gel. For purposes of this invention, the carrier shall be of sufficient viscosity to suspend the particles for sufficient duration to inject the composition.

BRIEF DESCRIPTION OF THE DRAWING

The FIG. 1 is a cross-sectional view of particles in accordance with the invention.

DETAILED DESCRIPTION OF THE PREFERRED EMBODIMENT

The invention consists of an injectable composition that is a combination of a plurality of small, randomly-shaped particles that are carried in a lubricative fluid or gel that is preferably comprised of a biologically compatible, lubricous solution, suspension, other fluid or gel.

The particles comprise a plurality of discrete, physiologically compatible, microbeads or microparticles of isotropic carbon of a predetermined size range and an improved lubricative fluid or gel in which the particles are carried. The carrier is a biologically compatible solution or suspension. The particles range in size from 90 to 1,000 microns in transverse, cross-sectional dimension.

The composition is designed to be delivered into the body through a small-bore needle, cannula, or catheter to a tissue site for the purpose of augmenting the tissue site and surrounding area, thereby correcting a defect, filling a void or strengthening the support structures of the tissue.

The invention is comprised of two components. The first is a plurality of isotropic carbon particles ranging in size as microbeads or microparticles from a minimum of 90 microns to a maximum of 1,000 microns. The preferred carbon is a low temperature isotropic (LTI) carbon. These isotropic carbon particles are created by a pyrolitic process. Pyrolytic derives from the term pyrolysis, which is a thermal decomposition of hydrocarbons in a process in which hydrocarbons and alloying gases are decomposed in a fluidized or floating bed. Inert gas flow is used to float the bed and a material (deposition material) onto which the low temperature isotropic pyrolytic carbon is deposited. The hydrocarbon pyrolysis results in a high carbon, low hydrogen solid material.

The atomic structure of pyrolytic LTI carbon is similar to graphite, the common form of carbon, but the alignment between hexagonal planes of atoms is not as well ordered. Pyrolytic carbon is characterized by a more chaotic atomic structure with warped hexagonal planes, missing atoms and generally a more turbostatic appearance resulting in better bonding between layer planes.

A hard, metallic or ceramic material capable of withstanding the high temperature conditions of the pyrolytic carbon deposition process is the preferred deposition material. Aluminum oxide, zirconium oxide and graphite have been found to be especially suitable as deposition material.

After the pyrolytic carbon deposition process is completed, the pyrolytic carbon is removed from the deposition material by milling, grinding or machining arranged to produce the desired particle size. This results in randomly sized and shaped pure pyrolytic carbon particles. The removed particles are subjected to a cleaning and sieving process that removes contaminants and separates out particles of a size greater than 90 microns or less than 1,000 microns in average, transverse cross-sectional dimensions, and a preferred size range between 200 and 300 microns. The preferred size avoids particle migration from the injection site and facilitates injection through a small bore instrument. The sieving process is such that the minimum particle dimension will pass through a U.S. No. 18 screen mesh, which has a 1000 micron grid size opening, but will not pass through a U.S. No. 170 screen mesh, which has a 90 micron grid size opening. The resulting minimum dimension of the particles is the transverse, cross-sectional dimension on oblong or elongated particles.

The high strength, resistance to breakdown or corrosion, and durability of the pyrolytic carbon insures the effective, long term functioning of the particles in tissue augmentation at the injection site. The established biocompatibility of pyrolytic carbon renders it particularly suitable for the anticipated body tissue applications.

The carrier is preferably an aqueous suspension or solution, other fluid or gel of polymeric chains of B-D-glucose, commonly referred to as B-glucan. The glucose units are linked to each other at the 1-3, 1-4, or 1-6 positions and form polymeric chains ranging to several thousand daltons in weight. The preferred B-glucan carrier is in combination with agarose to form a self-supporting gel.

B-Glucan is a naturally occurring constituent of cell walls in essentially all living systems including plants, yeast, bacteria, and mammalian systems. Its effects and modulating actions on living systems have been studied extensively (see Abel, G., and Czop, J. K., "Stimulation of Human Monocyte B-Glucan Receptors by Glucan Particles Induces Production of TNF-Gamma and iL-B", *Int. J. Immunopharmacol.,* 14 (8):1363–1373, 1992 and references included therein). B-glucan, when administered in experimental studies, elicits and augments host defense mechanisms including the steps required to promote healing by first intent, thereby stimulating the reparative processes in the host system. B-glucan is rapidly removed from tissue sites through macrophagic phagocytosis or by enzymatic destruction by serous enzymes. The rapid destruction or removal of B-glucan, as well as its available viscosity and lubricous nature, makes it an optimum carrier for the particles.

Aqueous solutions, suspensions, fluids, or gels of B-glucan can be produced that have favorable physical characteristics as a carrier for solid carbon or carbon-coated particles. The viscosity can vary from a thin liquid to a firm, self-supporting gel. Irrespective of viscosity, the B-glucan has excellent lubricity, thereby creating a particle-carrier composition which is easily administered by delivery to a predetermined body site through a small bore needle, cannula, or catheter. A preferred B-glucan composition is B-D glucan containing 4-0-linked-B-D-glycopyranosyl units and 3-0-linked-B-D-glycopyranosyl units in combination with agarose. The carrier will be of sufficient viscosity as a self-supporting gel to assure that the pyrolytic carbon particles remain suspended therein, for sufficient duration to complete the injection procedure.

Other examples of appropriate carriers are undiluted agarose, methyl cellulose or other linear unbranched polysaccharide. Further examples of appropriate carriers include hyaluronic acid, polyvinyl pyrrolidone or a hydrogel derived thereof, dextran or a hydrogel derivative thereof, glycerol, polyethylene glycol, succinylated collagen, liquid collagen, oil based emulsions such as corn oil or safflower, or other polysachaarides or biocompatible organic polymers either singly or in combination with one or more of the above-referenced solutions.

In use, the above-described composition will be injected through a syringe needle or cannula into a body tissue site. When deposited into a soft tissue site, the carrier gel will disperse over time. The particles are of an optimum size which will prevent their being carried away by capillary blood flow. They will thus remain at the site and will serve to fill voids, provide additional support, or correct the soft tissue defects.

The composition of the present invention may also be utilized in urological applications. The composition may be injected into the tissue of the urinary tract, wherein the selected site may be, for example, the mucosal tissue of the bladder neck, the urethra or urethral sphincter. The resulting bulking or augmentation of the urethral tissue will restrict the size of the urethra or urinary passage and thus assist in overcoming incontinence.

The present composition is also useful in fecal or anal incontinence applications. The composition may be injected into the tissue of the anal canal, wherein the selected site may be, for example, the mucosal tissue of the anal canal, for example, near the internal or external anal sphincter muscle. The resulting bulking or augmentation of the urethral tissue will restrict the size of the sphincter or anal passage and thus assist in overcoming fecal or anal incontinence.

Applicants also believe the present composition can be utilized in gastroesophageal reflux (GER) applications. The composition may be injected into the mucosal tissue of the upper gastrointestinal tract, wherein the selected site may be, for example, the mucosal tissue of the cardiac orifice of the stomach, which opens into the esophagus. The resulting bulking or augmentation of the tissue will restrict the size of the passage and thus assist in overcoming gastric fluids refluxing into the esophagus.

A number of devices are currently in use for soft tissue augmentation. The Lawin U.S. Pat. No. 5,792,478 patent discusses pure carbon beads, with either graphite or pyrolytic carbon substrate material, which is coated with pyrolytic carbon to form a pure carbon bead and a B-glucan carrier gel. The present invention is unique in that pure pyrolytic carbon is the preferred particle, rather than a pyrolitic carbon substrate, and that the carrier gel preference is B-glucan with the addition of agarose, which is added to form a self supporting gel.

Numerous other characteristics and advantages of the present invention have been set forth in the foregoing description. It will be understood, however, that this disclosure is, in many respects, merely illustrative. Changes may be made in details, particularly in matters of shape, size and arrangement of parts without exceeding the scope of the invention.

Therefore, while this invention has been described with reference to an illustrative embodiment, this description is not intended to be construed in a limiting sense. Various modifications of the illustrative embodiment, as well as other embodiments of the invention, will be apparent to persons skilled in the art upon reference to this description. It is therefore contemplated that the appended claims will cover any such modifications or embodiments as fall within the true scope of the invention.

What is claimed is:

1. An injectable, bioicompatible composition for tissue augmentation comprising:
a plurality of discrete microscopic isotropic carbon particles in a carrier, each of said particles being manufactured by removing isotropic carbon from a deposition material selected from a compound selected from the group consisting of aluminum oxide, zirconium oxide and graphite, said particles having an average transverse cross sectional dimension of between 90 and 1,000 microns, further, and wherein the carrier is a biocompatible medium having sufficient fluidity to carry and deliver the particles, and has lubricative qualities.

2. The composition of claim 1 wherein said particles are of rounded shape and said dimension is between 200 microns and 300 microns.

3. The composition of claim 1 wherein the carrier is B-glucan in combination with an adequate quantity of agarose to form a self-supporting gel.

4. An injectable, biocompatible composition for tissue augmentation comprising:
a plurality of discrete microscopic isotropic carbon particles in a carrier, said particles having an average transverse cross sectional dimension of between 90 and 1,000 microns and the carrier is a biocompatible medium having sufficient fluidity to carry and deliver the particles, and has lubricative qualities.

5. The composition of claim 4 wherein the carrier is B-glucan in combination with an adequate quantity of agarose to form a self-supporting gel.

6. An injectable, biocompatible composition for tissue augmentation comprising:
a plurality of discrete particles in a carrier, wherein the particles are isotropic carbon particles and have an average transverse cross sectional dimension of between 90 and 1,000 microns and the carrier is a biocompatible medium having sufficient fluidity to carry and deliver the particles, where in said carrier is B-glucan in combination with an adequate quantity of agarose to form a self-supporting gel.

7. A method for augmenting tissue in a human patient comprising injecting into a tissue site in the patient a composition comprising a plurality of discrete isotropic carbon particles having an average, transverse, cross-sectional dimension of between 90 and 1,000 microns in a biocompatible carrier having sufficient fluidity to carry and deliver the particles and has lubricative qualities, wherein the tissue site is the coronary orifice to the stomach.

8. The method of claim 7 wherein said carrier is B-glucan in combination with an adequate quantity of agarose to form a self-supporting gel.

9. A method for augmenting tissue in a human patient comprising injecting into a tissue site in the patient a composition comprising a plurality of discrete isotropic carbon particles having an average, transverse, cross-sectional dimension of between 90 and 1,000 microns in a biocompatible carrier having sufficient fluidity to carry and deliver the particles and has lubricative qualities, wherein the tissue site is the anal canal.

10. The method of claim 9 wherein said carrier is B-glucan in combination with an adequate quantity of agarose to form a self-supporting gel.

11. The method of claim 9 wherein the tissue site is the internal sphincter muscle of the anal canal.

12. The method of claim 10 wherein the tissue site is the internal sphincter muscle of the anal canal.

13. The method of claim 9 wherein the tissue site is the internal sphincter muscle of the anal canal.

14. The method of claim 10 wherein the tissue site is the internal sphincter muscle of the anal canal.

15. The method of claim 9 wherein said substrate particles are of random shape and said dimension is between 200 microns and microns.

16. The method of claim 10 wherein said substrate particles are of random shape and said dimension is between 200 microns and microns.

17. A method for augmenting tissue in a human patient comprising injecting into a tissue site in the patient a composition comprising a plurality of discrete isotropic carbon particles having an average, transverse, cross-sectional dimension of between 90 and 1,000 microns in a biocompatible carrier having sufficient fluidity to carry and deliver the particles and has lubricative qualities, wherein the tissue site is the urinary tract.

18. The method of claim 17 wherein said carrier is a B-glucan in combination with an adequate quantity of agarose to form a self-supporting gel.

19. The method of claim 17 wherein said substrate particles are of random shape and said dimension is between 200 microns and 300 microns.

20. The method of claim 18 wherein said substrate particles are of random shape and said dimension is between 200 microns and 300 microns.

* * * * *